United States Patent [19]

Magnuson et al.

[11] Patent Number: 4,896,667
[45] Date of Patent: Jan. 30, 1990

[54] ENDOTRACHEAL TUBE BITE BLOCK

[76] Inventors: Linda M. Magnuson, 2357 N. 193rd St., Seattle, Wash. 98155; Dwight W. Roxburg, 3615 Greenwood Rd., Sedalia, Colo. 80135

[21] Appl. No.: 265,899

[22] Filed: Nov. 2, 1988

[51] Int. Cl.⁴ .................... A61B 24/00; A61M 25/00; A61M 16/00
[52] U.S. Cl. .......................... 128/207.14; 128/207.17; 128/DIG. 26
[58] Field of Search ...................... 128/207.14, 207.17, 128/912, DIG. 26, 200.26, 201.26, 911, 206.29, 207.15

[56] References Cited

U.S. PATENT DOCUMENTS

| | | | |
|---|---|---|---|
| 4,167,946 | 9/1979 | Sandstrom | 128/207.17 |
| 4,331,143 | 5/1982 | Foster | 128/DIG. 26 |
| 4,344,428 | 8/1982 | Sherman | 128/207.14 |
| 4,640,273 | 2/1987 | Greene et al. | 128/207.14 |

*Primary Examiner*—David A. Wiecking
*Assistant Examiner*—Kimberly L. Asher
*Attorney, Agent, or Firm*—Douglas E. Winters

[57] ABSTRACT

An endotracheal tube bite block of simple design which can be secured to a standard endotracheal tube, the block and tube anchored reliably with an attachment strap so that bodily shifting of the tube within the trachea is deterred. Two embodiments of the instant bite block have an elongated hard core of generally C-shaped cross-section and a material not as hard as the core, the softer material being secured to a portion of the exterior of the hard core, and a portion of the hard core being exposed. The bite block can be secured to a standard endotracheal tube by taping the exposed portion of the hard core to the tube. Preferably, the bite block has two radial apertures through the softer material and the hard core to permit securing of the bite block and tube to a patient with a flexible strap. It may be possible to attach the bite block and tube with an attachment strap threaded through a transverse aperture in the softer material and hard core or otherwise attached to the bite block. In a third embodiment, the bite block is made from a single material, such as PVC having a 65 durometer hardness. A radial aperture and/or transverse grooves may be provided to the third embodiment to engage a neck strap.

19 Claims, 3 Drawing Sheets 4,896,667

ENDOTRACHEAL TUBE BITE BLOCK

TECHNICAL FIELD

The present invention relates to endotracheal tube bite blocks and, more particularly, to a bite block which may be secured to an endotracheal tube and the bite block and attached endotracheal tube anchored to a patient with a flexible attachment strap.

BACKGROUND ART

Endotracheal tubes are intubated, i.e., inserted into the trachea, to provide a clear passage for air to the lungs if the trachea has been crushed in an automobile accident, for example. Also, a tube may be intubated prior to anesthetizing a patient with a general anesthetic to maintain a clear air passage in case the trachea collapses due to relaxation of the muscles supporting the trachea.

Endotracheal tubes may be intubated through the mouth, designated an oral endotracheal tube; through the nose, designated a nasal endotracheal tube; or through the tracheostomy incision in the front of the neck and trachea, designated a tracheostomy tube. In an emergency situation an oral endotracheal tube is normally used to provide an air passage to the lungs. After the patient's condition has been stabilized, which may require a week or more, the oral endotracheal tube is removed, a tracheostomy incision is made in the neck and trachea, and a tracheostomy tube is intubated through the tracheostomy incision to provide the air passage.

The tubes also may include an inflatable endotracheal balloon or cuff which surrounds and is fixed to the outer surface of the tube adjacent to its lower end. After the tube is inserted into the trachea, the bulb-shaped cuff is inflated with air through a small diameter tube connected to the cuff interior and which runs upward along the tube to the external portion of the tube. The inflated cuff seals the space between the endotracheal tube and tracheal wall, preventing air from escaping from the lungs past the exterior of the tube and preventing saliva and other liquids from draining into the lungs.

The trachea can be stretched and permanently deformed if the cuff is overinflated. Therefore, as the cuff is inflated, passage of air past the cuff is monitored using a stethoscope. When passage of air ceases inflation of the cuff is stopped. The pressure exerted by the cuff against the tracheal wall is sufficient to prevent movement between the cuff and the tracheal wall.

Since the trachea in children is not as pliable as in an adult, an inflated cuff could more easily stretch and permanently deform the trachea of a child. Therefore, pediatric endotracheal tubes do not include inflatable cuffs and the space between the tube and the trachea must be suctioned frequently to deter saliva from collecting in the lungs.

To insure that the tube is not inserted so far that the lower end is within one of the mainstem bronchi causing one of the lungs not to inflate, bilateral chest excursion, i.e., movement of both sides of the chest during breathing, is observed. To verify the location of the lower end of the tube within the trachea, an x-ray opaque color strip may be incorporated along the length of the tube. After the tube is inserted into the lumen of the trachea, the cuff is inflated, the tube is anchored in place and proper positioning of the tube is verified by x-ray photography.

The length of the endotracheal portion of the tube, i.e., the amount of tube which is inserted into the patient's trachea, is dependent on the length of the patient's trachea and, in the case of a tracheostomy tube, the location of the tracheostomy incision. The tube should be intubated to the proper depth, namely past the tracheal blockage in the case of a crushed trachea and preferably until the lower or distal end of the tube is within a few centimeters of the bronchial bifurcation of the trachea, i.e., just above the right and left main stem bronchi, whether there is a tracheal blockage or the patient is to be anesthetized. The length of the tube projecting outward from the mouth or neck incision of the patient is dependent on the length of the endotracheal portion.

Once the endotracheal tube, whether an oral tube or a tracheosotmy tube, has been intubated to the proper depth, it must be anchored to the patient to prevent accidental withdrawal of the tube causing possible asphyxiation due to collapse of the trachea and to prevent further insertion of the tube past the bronchial bifurcation. Since the trachea lengthens and contracts as the patient breathes, there will always be some relative movement between the endotracheal tube cuff and the trachea. Such movement causes scar tissue to form which thickens the wall of the trachea. By anchoring the exterior portion of the tube stationarily such movement is minimized.

Since the tubes are made of pliant material and a comatose patient may bite down on an oral endotracheal tube so that the lumen or passage through the tube is constricted, a bite block may be inserted between the upper and lower teeth of the patient when an oral endotracheal tube is used. A typical bite block consists of a relatively hard material which either surrounds the tube or has a thickness approximately equal to the diameter of the tube. Roxburg et. al. U.S. Pat. No. 4,527,559 discloses bite blocks having an elongated hard core which is encapsulated in a block of material not as hard as the core. The block has at least one transverse aperture through which a flexible strip is threaded. The strip is also threaded through a transverse aperture in a specialized endotracheal tube and tied around the patient's neck.

Eross U.S. Pat. No. 3,946,742 discloses a bite block including a retainer having a slotted channel into which an oral endotracheal tube is inserted. The bite block is secured to the endotracheal tube by wrapping an elastic strap which is secured to the bite block around the endotracheal tube and engaging a selected hole in a strap with a post on the bite block. An attachment strap, permanently secured to the bite block, is wrapped around the neck and secured to a post on the bite block. The retainer may be covered with a softer protective layer. The tube is not anchored reliably because the strap around the tube may slip, particularly if it is moistened by saliva, allowing the longitudinal position of the tube within the trachea to change.

Sandstrom U.S. Pat. No. 4,167,946 discloses a bite block having a slotted cylindrical support member into which an endotracheal tube is inserted and a tubular teeth shield member having an internal diameter greater than the external diameter of the endotracheal tube. The bite block also has a radial aperture through which a flexible strip is threaded and used to tie the block to the tube and to the patient. Again the strap when tied around the tube may slip when moistened with saliva.

Sheridan et. al. U.S. Pat. No. 3,973,569 discloses a tracheostomy tube assembly which comprises a tube having a flexible, transversely elongated, fixed flange at the proximal or upper end of the tube; a flexible transversely elongated, slidable flange between the fixed flange and the patient's neck; and a plurality of detachable split rings positioned between the two flanges. As shown in FIG. 3 of the Sherman et. al. reference, the assembly is anchored to the patient's neck by a strap inserted through slots in the outer ends of the fixed and slidable flanges with the slidable flange abutting the patient's neck. By inserting a greater number of split rings between the two flanges, the portion of the tube extending out away from the patient's neck is increased and the endotracheal portion is shortened. The Sheridan et. al. assembly is objectionable because it is complex comprising numerous parts and the range of tube penetration which may be selected is limited to about 3 centimeters.

The tracheostomy tube retainer disclosed in the McGinnis U.S. Pat. No. 3,987,798 surrounds the upper end of the tube and is banded to the patient's neck by a strap extending through slots in the retainer. The retainer includes a pair of opposed struts which project outwardly perpendicular to the patient's neck and have a plurality of slots spaced longitudinally along the struts. The upper or external end of the tube has a pair of opposed lateral tabs which project transversely outward from the tube. Each tab is inserted into a slot in one of the struts to secure the tube to the retainer. The penetration of the McGinnis tracheostomy tube is established by inserting the tabs into the desired slots in the retainer struts. The McGinnis assembly has an undesirably large number of interacting parts. Further the retainer permits only about a 4 cm variation in the endotracheal length and the retainer struts project some 5 cm outwardly from the patient's neck.

The tracheostomy tube assembly of the Ranford et. al. U.S. Pat. No. 4,235,229 includes a tracheostomy tube and a neck collar which has an outstanding deformable sleeve. The collar is strapped around the patient's neck with a tie. The outer end portion of the tube, which has a plurality of ribs, protrudes through the outstanding collar sleeve. A pair of lugs on the outer end of the sleeve projects transversely inward and engages the tube between the ribs to anchor the tube. The range of endotracheal length is limited to about 2.5 cm.

The clamps disclosed in Andrew U.S. Pat. Nos. 3,602,227 and 3,760,811, and Nestor et. al. U.S. Pat. No. 4,249,529 encircle and grip an endotracheal tube. Such clamps are strapped around the neck and/or head of the patient with attachment straps. Since the tube is made of flexible material which becomes slippery when moistened, it may slip relative to the clamp.

In the Schultz U.S. Pat. No. 3,927,676 and Arrott U.S. Pat. No. 3,713,448, oral endotracheal tubes are held with adhesive tape. However, in repositioning and retaping the tube at least daily, repeated stripping of adhesive tape skins the patient's face.

In summary, the tracheostomy tube attachment mechanisms of the prior art are complex, having numerous parts, and the range of selectable endotracheal length is too limited or require special endotracheal tubes. None of the prior art suggests a bite block with a hard core having a portion enclosed in a softer material and an exposed portion to permit securing of the bite block to an endotracheal tube with adhesive tape. Further, none of the prior art suggests a bite block having a hard core with an aperture for attachement of the bite block and tube to a patient.

SUMMARY OF THE INVENTION

It is an object of the present invention to provide an endotracheal tube bite block of simple design which can be secured to a standard endotracheal tube, and the block and tube anchored reliably with an attachment strap so that bodily shifting of the tube within the trachea is deterred.

Such object can be accomplished by a bite block having an elongated hard core of generally C-shaped cross-section and a material not as hard as the core, the softer material being secured to a portion of the exterior of the hard core, and a portion of the hard core being exposed. The bite block can be secured to a standard endotracheal tube by taping the exposed portion of the hard core to the tube.

Preferably, the bite block has two radial apertures through the softer material and the hard core to permit securing of the bite block and tube to a patient with a flexible strap. It may be possible to attach the bite block and tube with an attachment strap threaded through a transverse aperture in the softer material and hard core or otherwise attached to the bite block.

DETAILED DESCRIPTION OF THE INVENTION

Figure 1:
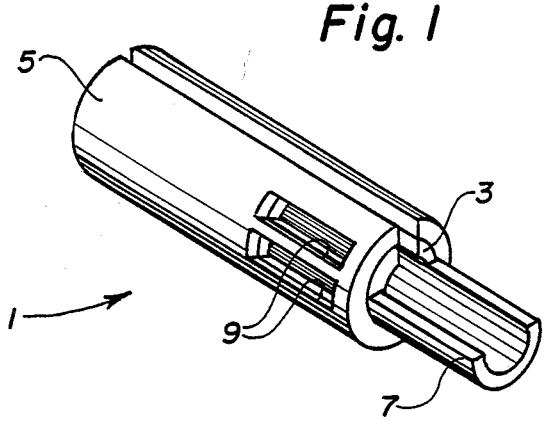
FIG. 1 is a front perspective of a bite block in accordance with the present invention.
Figure 2:
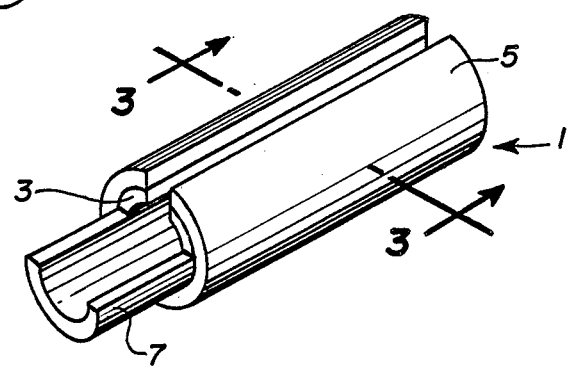
FIG. 2 is a back perspective of the FIG. 1 bite block.
Figure 3:
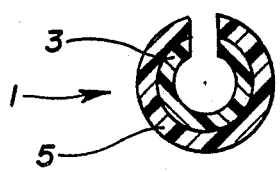
FIG. 3 is a transverse section taken on line 3—3 of FIG. 2.
Figure 4:
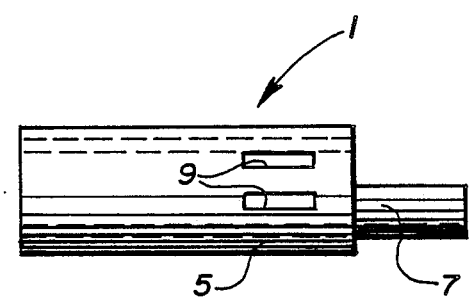
FIG. 4 is a side elevation of the FIG. 1 bite block.

The bite block 1 shown in FIGS. 1 to 4 includes two components. The generally C-shaped cross-section core 3 is a hard plastic material. The inner diameter of the hard core is preferably the same or slightly less than the outer diameter of the standard endotracheal tube to which the bite block is to be attached. Therefore, when the bite block is slipped on to the endotracheal tube the position of the bite block on the tube is maintained by a friction fit.

The phrase "generally C-shaped cross-section" is intended to include cross-sections having a concave side. The side may be of U- or V-shape or only a portion of the side may be concave. The remaining sides form a generally convex surface which may be curved or composed of generally flat surfaces with rounded or angular corners.

A material 5 not as hard as the hard core, such as a pliable poly-vinyl chloride, is secured to a portion of the exterior surface of the core. The purpose of the softer material is to protect the teeth of the patient and to make the bite block more comfortable to the patient.

To ensure positive attachment of the bite block to the tube, a portion 7 of the hard core is not covered by the softer material but is let exposed. This exposed portion is secured to the tube with adhesive tape. Preferably, the portion is approximately semicircular in cross-section so that a substantial portion of the tube is exposed to the adhesive tape.

The bite block and attached tube are secured to the patient by a flexible attachment strap, such as twill tape, by threading the attachment strap through an aperture or apertures in the softer material and hard core of the bite block and tying around the neck of the patient. Preferably, the bite block has two radial apertures 9 through which the twill tape is threaded.

To keep the twill tape below the interior of the hard core, the interior termini of the aperture may be connected by a groove. If the hard core and softer material are sufficiently thick, the bite block could have a single transverse aperture through which the twill tape can be threaded.

Figure 5:
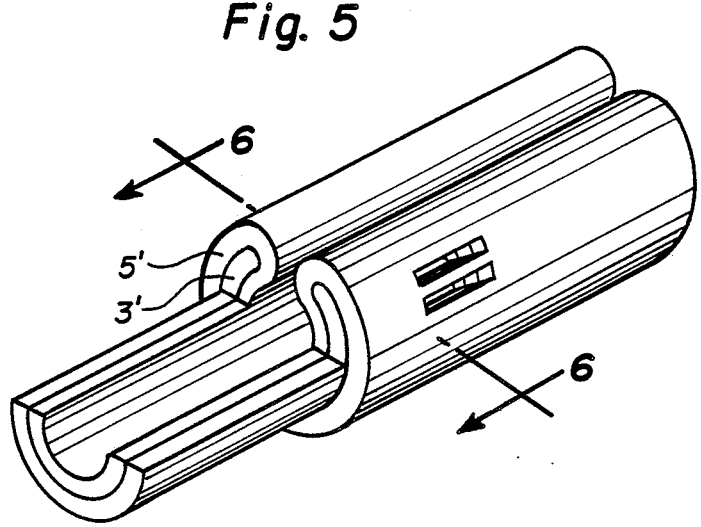
FIG. 5 is a front perspective of a second embodiment of the bite block in accordance with the present invention.
Figure 6:
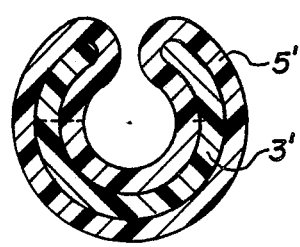
FIG. 6 is a transverse section taken on line 6—6 of FIG. 5.
Figure 7:
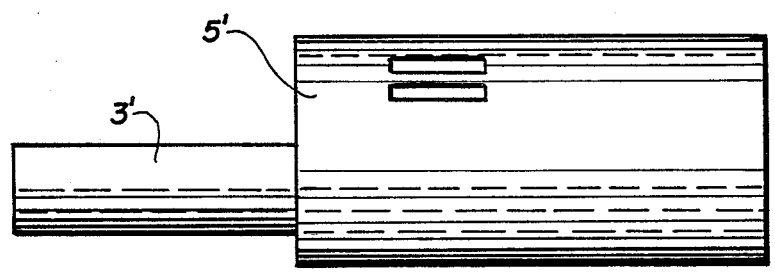
FIG. 7 is a side elevation of the FIG. 5 bite block.

In a second embodiment, the softer material is secured to the interior and exterior surfaces of the hard core as shown in FIGS. 5-7. In this embodiment, the softer material 5' encloses a portion of the hard core 3'.

Figure 8:
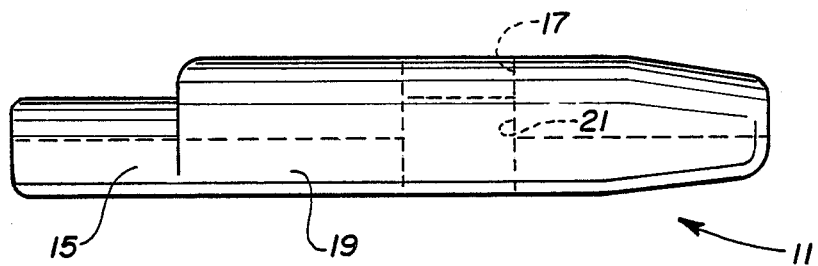
FIG. 8 is a side elevation of a third embodiment of the bite block in accordance with the present invention.
Figure 9:
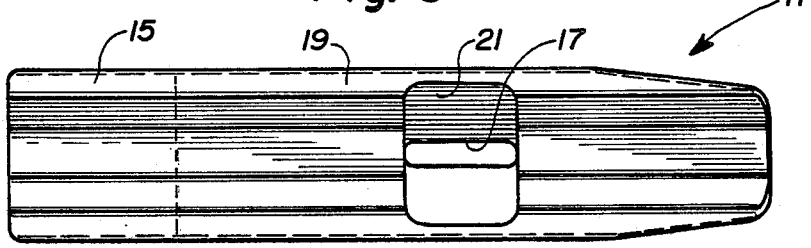
FIG. 9 is a bottom plan view of the FIG. 8 bite block.
Figure 10:
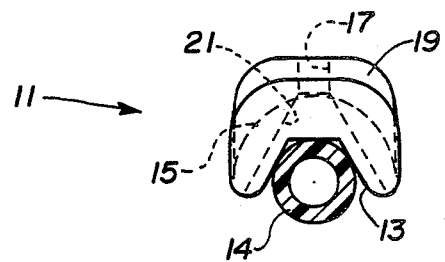
FIG. 10 is an end view of the FIG. 8 bite block.

In a third embodiment shown in FIGS. 8-10, the endotracheal tube bite block is made from a single material, such as poly-vinyl chloride having a 65 durometer hardness. Such a material has sufficient stiffness to prevent collapse of the endotracheal tube, but pliable enough to be relatively comfortable to the patient. Being of a single material, mold manufacturing is simplified.

As in the previous embodiments, the bite block 11 is generally C-shaped in cross-section throughout the entire length of the bite block. The concave surface 13 is placed adjacent the endotracheal tube 14. As shown in FIG. 10, the reentrant side of the bite block surrounds less than one half of the circumference of the endotracheal tube. Therefore, a major portion of the endotracheal tube circumference is exposed to enable good securement of the bite block to the tube with adhesive tape. In all three of the embodiments shown the portion of the bite block which is taped to the tube is generally semicircular in cross-section.

Rather than an exposed portion of a hard core, the bite block II has an end portion 15 of reduced thickness which may be secured to the endotracheal tube by adhesive tape, for example. Of course, the reduced thickness is not necessary, but a substantial portion of the endotracheal tube must be exposed to permit positive securement of the bite block to the tube.

A radial aperture 17 is located in the thicker portion 19 of the bite block. Preferably the aperture is near the middle of the thicker portion. A flexible strip such as twill tape is threaded through the radial aperture, between the interior surface of the bite block and the exterior surface of the endotracheal tube, and tied around the neck of the patient.

It is preferred to have a transverse groove 21 extending from the interior terminus of the radial aperture, along the interior surface on each side of the bite block. By this means, a twill tape threaded through the radial aperture from the exterior terminus will run along the exterior surface of the endotracheal tube in one of the transverse grooves, and then it can be tied around the neck of the patient.

It may be found desirable to thread the twill tape through the radial aperture along the exterior of the endotracheal tube in one transverse groove, around the endotracheal tube, up the opposite side of the endotracheal tube in the other transverse groove and up the radial aperture from the interior terminus. The twill tape can then be tied off to secure the bite block to the endotracheal tube, and then the twill tape tied around the neck of the patient.

We claim:

1. A bite block for use with an endotracheal tube, said bite block comprising teeth-engaging means and endotracheal tube-engaging means, said tube-engaging means comprising an elongated hard core of generally C-shaped cross-section, said hard core having both a proximal end portion and a distal end portion, said teeth-engaging means comprising a covering of material softer than said hard core, said covering being secured to the exterior surface of said hard core only at said proximal end portion.

2. The bite block according to claim 1, wherein the distal end portion of the hard core is C-shaped and has a curvature of 180 degrees or less.

3. The bite block according to claim 1, wherein the proximal end portion of the hard core further comprises receiving means for receiving a flexible strap, said receiving means having a radial aperture extending from the exterior surface of the covering to the interior surface of the hard core.

4. The bite block according to claim 3, wherein the receiving means has a second radial aperture extending from the exterior surface of the covering to the interior surface of the hard core.

5. The bite block according to claim 4, wherein the receiving means has a groove extending between and connecting the two radial apertures along the interior surface of the hard core.

6. The bite block according to claim 1, wherein the cover extends along both the exterior and interior surfaces of the proximal end of the hard core and along the interior surface of the distal end portion of the hard core.

7. The bite block according to claim 1, wherein the cover does not extend along the interior surfce of the hard core.

8. A bite block for use with an endotracheal tube, said bite block being of generally C-shaped cross-section through out its length and having an exterior surface and an interior surface, the bite block comprising receiving means for receiving a flexible strap and having a groove transverse to the elongated axis of the bite block, said receiving means having a radial aperture extending from the exterior surface of the bite block to the interior surface of the bite block, the groove extending from the interior terminus of the radial aperture along the interior surface of the bite block.

9. The bite block according to claim 8 having a second transverse groove extending from the interior terminus of the radial aperture along the interior surface of the bite block opposite the first groove.

10. The bite block according to claim 8, wherein the bite block is a single piece of polyvinyl chloride material having a hardness of about 65 durometer.

11. The bite block according to claim 8, wherein the bite block has a distal end portion of reduced thickness.

12. A bite block for use with an endotracheal tube having an elongated axis, said bite block having a cross section defined by a single generally C shaped member comprising an exterior generally convex surface and an interior generally concave surface;

said interior and exterior surfaces extending generally parallel to the elongated axis, the exterior surface acting as teeth-engaging means, the interior surface acting as endotracheal tube engaging means;

wherein the cross section of the interior concave surface is such that the length of a line segment across the mouth of the concave surface is greater than the length of any other line segment parallel to the first line segment and having end points on the concave surface.

13. The bite block according to claim 12, having an aperature extending from the exterior surface of the bite block to the interior surface of the bite block.

14. The bite block according to claim 13 having a groove extending from the interior terminus of the aperture along the surface of the reentrant side.

15. The bite block according to claim 14 having a second groove extending from the interior terminus of the aperture along the surface of the reentrant side opposite the first groove.

16. The bite block according to claim 12, wherein the bite block is a single piece of polyvinyl chloride material having a hardness of about 65 durometer.

17. The bite block according to claim 12, wherein the bite block has a distal end portion of reduced thickness.

18. The bite block according to claim 12, wherein the concave surface is generally V-shaped in cross-section.

19. The bite block according to claim 18, wherein the V-shape has a generally flat bottom.

* * * * *